United States Patent
Parker et al.

(10) Patent No.: US 6,458,091 B1
(45) Date of Patent: Oct. 1, 2002

(54) MUSCLE TONE REDUCTION SPLINT

(76) Inventors: Deborah Sue Parker, 1656 Edgewood Dr., Caro, MI (US) 48723; Kristine Bellenbaum, 11457 Lake Circle Dr., Saginaw, MI (US) 48609

( * ) Notice: Subject to any disclaimer, the term of this patent is extended or adjusted under 35 U.S.C. 154(b) by 0 days.

(21) Appl. No.: 09/583,156

(22) Filed: May 30, 2000

(51) Int. Cl.[7] ................................ A61F 5/00; A61F 5/37
(52) U.S. Cl. ............................ 602/21; 602/22; 602/62; 128/879
(58) Field of Search .................... 602/5, 20–22, 602/30, 60–62, 64; 128/878–879; 2/16–18, 20, 160, 161.1, 161.2, 163; 482/24, 48–49; 295/25; 473/59, 61–62

(56) References Cited

U.S. PATENT DOCUMENTS

| 3,606,343 | A | * | 9/1971 | Lemon | 273/189 |
|---|---|---|---|---|---|
| 4,552,359 | A | * | 11/1985 | McDonald | 473/61 |
| 4,558,694 | A | * | 12/1985 | Barber | 602/21 |
| RE32,287 | E | * | 11/1986 | Willis | 2/16 |
| 4,777,666 | A | * | 10/1988 | Beverlin | 2/161.5 |
| 4,984,300 | A | * | 1/1991 | Cho | 2/18 |
| 5,781,928 | A | * | 7/1998 | Avila | 2/16 |
| 6,119,267 | A | * | 9/2000 | Pozzi | 2/20 |
| 6,238,357 | B1 | * | 5/2001 | Kawaguchi et al. | 601/27 |

* cited by examiner

Primary Examiner—Denise M. Pothier
(74) Attorney, Agent, or Firm—Reising, Ethington, Barnes, Kisselle, Learman & McCulloch, P.C.

(57) ABSTRACT

The muscle tone reduction splint has an elongated pad. A retainer strap holds the pad against the sole of the foot or the palm of a hand adjacent to the digits. A plurality of digit separators are secured to the elongated pad. A free end of each digit separator is secured to hold the digit separators between adjacent digits. Securing the digit separators promotes a reduction of muscle hypertonicity in the extremities of neurologically impaired patients.

11 Claims, 3 Drawing Sheets

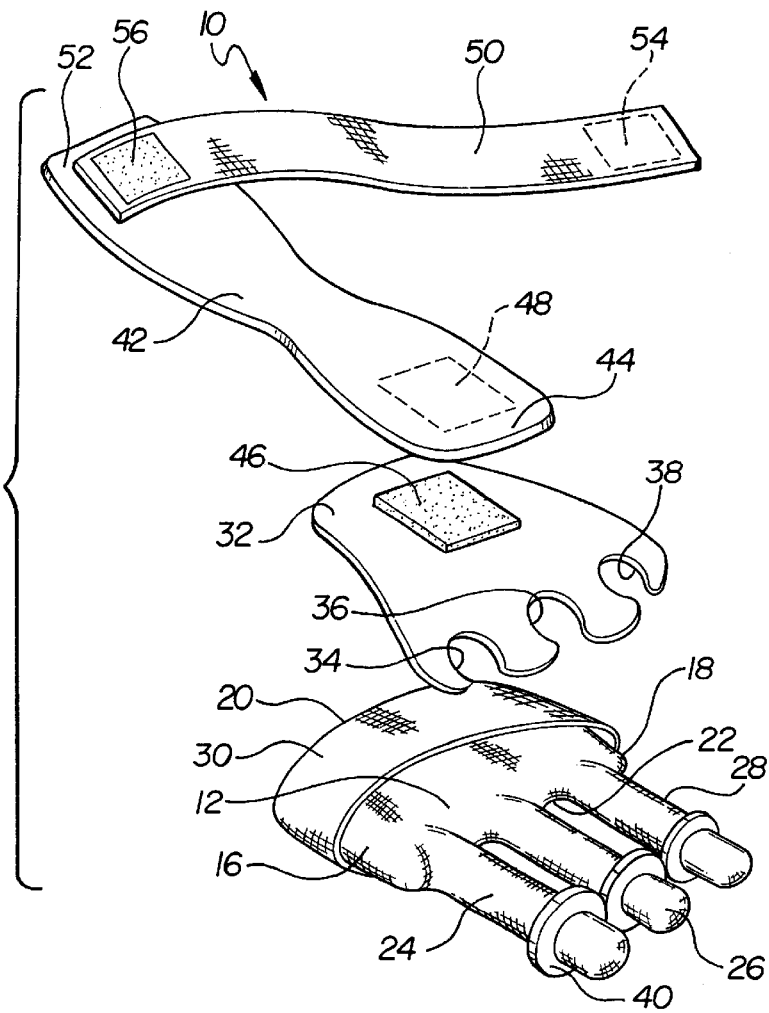
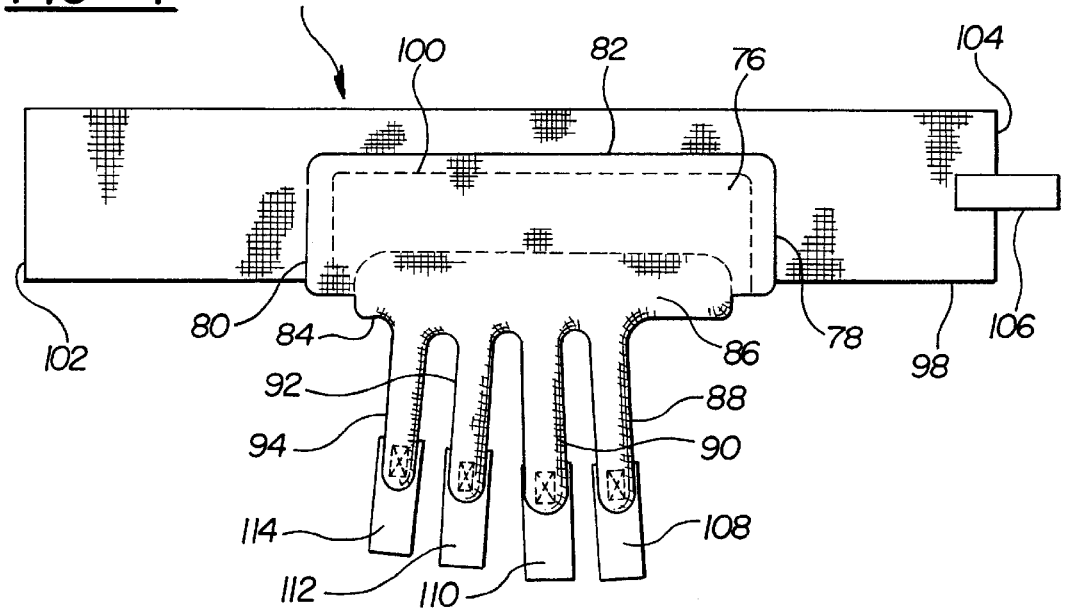

MUSCLE TONE REDUCTION SPLINT

TECHNICAL FIELD

The invention relates to maintaining the hand and or foot in reflex inhibiting positions to reduce hypertonicity. (increased muscle tone)

BACKGROUND OF THE INVENTION

Individuals with hypertonicity are at risk of developing joint contractures. splinting is designed to avoid the formation of contractures or control contractures that are already present. Muscles are stretched and elongated through therapy. Muscle length needs to be maintained following therapy. The use of a splint fabricated of a rigid thermoplastic material is ineffective with hypertonic individuals because it is nearly impossible to maintain complete contact between the hand and/or foot and the rigid thermoplastic splint. The thermoplastic splint does not allow for the movements that are obligatory in the upper and lower extremities due to primitive reflex patterns.

Many types of rigid splints have been used in an attempt to control contracture. These splints have generally not prevented wrist and finger contractures or toe grasp in the neurologically impaired patient. Continuous stretch with use of these rigid splints does not elicit the desired response of decreased tone and increased range of motion. Most thermoplastic splints are of volar design. Splinting the volar surface stimulates the flexor muscle group increasing the already excessive flexor tone in both the hand, wrist and/or ankle, foot. Often, patients complain of discomfort and do not tolerate rigid splints.

SUMMARY OF THE INVENTION

The Metacarpal, Phalangeal, Interphalangeal, Abduction, Extension, Wrist Extension, Mobilization, Muscle Tone Reduction Splint, Type 0 reduces hypertonicity in the hand and/or wrist. The Metatarsal Abduction, Mobilization, Muscle Tone Reduction Splint, Type 0 reduces hypertonicity in the toes, foot and ankle. Traditionally, preserving the longitudinal and palmar arches to provide functional hand position is the goal of splinting. However, in the severely, neurologically impaired patients with hypertonicity, there is little functional hand use. Issues with this population include: 1.Increased tone in wrist and finger flexors and finger adductors 2. Increased risk of contracture development 3. Skin integrity and 4. poor hygiene. Flattening of the palmar and longitudinal creases promote finger abduction. Finger abduction will relax the hand and reduce hypertonicity throughout the hand and wrist. Hypertonicity is decreased when tone in the Lumbricale and Palmar interossei muscle groups is reduced. Tone in the wrist and hand is reduced when the Lumbricale and Palmar interossei muscles are held in a prolonged passive stretch, while stabilizing the metacarpophalangeal joints. Relief of hypertonicity in the hand and wrist is the goal of the METACARPAL, PEALANGEAL, INTERPEALANGEAL, ABDUCTION, EXTENSION, WRIST EXTENSION, MOBILIZATION, MUSCLE TONE REDUCTION SPLINT, TYPE 0 .

When used on the hand, our device incorporates a fiber filled palm and finger cushion with a thermoplastic dorsal stabilization lid. The cushion is covered with a soft absorbent material to maintain good skin hygiene; the fiber allows air to pass through the cushion to the patient's hand. The cushion is gently positioned into the patient's palm, the flared end of the cushion is placed in the thumb web space. The three abductor pads that extend from the cushion are pulled between the index and middle finger, the middle and ring finger and the ring and the little finger. The dorsal stabilization lid provides metacarpophalangeal joint stability and ensures the finger cushion placement. The dorsal lid has a relieved area over the metacarpophalangeal joints to prevent skin breakdown and promote comfort.

Locking mechanisms between each finger allow the abductor pads to be secured into the dorsal lid at the metacarpophalangeal web space. A band attached to both ends of the palmar cushion is placed under the dorsal lid. If the inferior end of the dorsal lid requires stabilization, it can be anchored to the band secured to the palmar cushion. If necessary, a dorsal wrist and forearm component may be added to address excessive wrist flexion. This is also made of thermoplastic material. It is attached at the base of the dorsal lid. It crosses the wrist joint, covering ¾ the length of the forearm. It is secured at the distal portion with webbing.

Hypertonicity in the foot is characterized by a lower extremity extensor pattern, with increased tone in the toe, ankle and foot. The inversion reflex is triggered by pressure over the fifth metatarsal head. Pressure to the entire plantar surface of the metatarsal heads can result in toe grasp. The toe grasp reflex is demonstrated by marked increase of tone in the toe flexors and ankle plantarflexors. Relief of the toe grasp reflex as well as inversion and eversion reflex at the ankle is the goal of the Metatarsal, Mobilization, Muscle Tone Reduction Splint, Type 0.

The foot splint incorporates a resilient core material encased in an absorbent covering, secured with a series of hook and loop fastener. The device is placed under the ball of the foot with the metatarsal heads and lessens tactile and proprioceptive input into reflexogenous areas of the foot in the neurologically impaired patient. Hypertonicity is decreased when tone in the Interossei muscle group is reduced. Tone in the ankle and foot is reduced when the abductor muscles of the toes are held in a prolonged passive stretch while stabilizing the metatarsophalangeal joint. The soft strap that extends from the metatarsal roll is connected with a hook and loop fastener across the dorsum of the foot, just distal to the metatarsal heads. The four abductor pads that extend from the metatarsal roll are gently positioned between the great toe and the second toe, the second toe and the third toe, and the third toe and the fourth toe. Each abductor cushion is attached to the dorsal strapping using hook and loop fastener. The toes are held in abduction and the metatarsal joints are stabilized. This decrease of abnormal muscle tone, results in: decreased medial or lateral deviation of the forefoot which reduces toe grasp, reduction in inversion or eversion at the ankle and a decrease in ankle plantar flexor tone. When used in combination with an ankle foot orthosis, there is further tone reduction throughout the lower portion of the leg.

BRIEF DESCRIPTION OF THE DRAWINGS

The presently preferred embodiment of the invention is disclosed in the following description and in the accompanying drawings, wherein:

FIG. 3 is an expanded perspective view of the hand splint;

FIG. 4 is a bottom plan view of a foot splint;

DETAILED DESCRIPTION OF THE PREFERRED EMBODIMENTS

Figure 1:
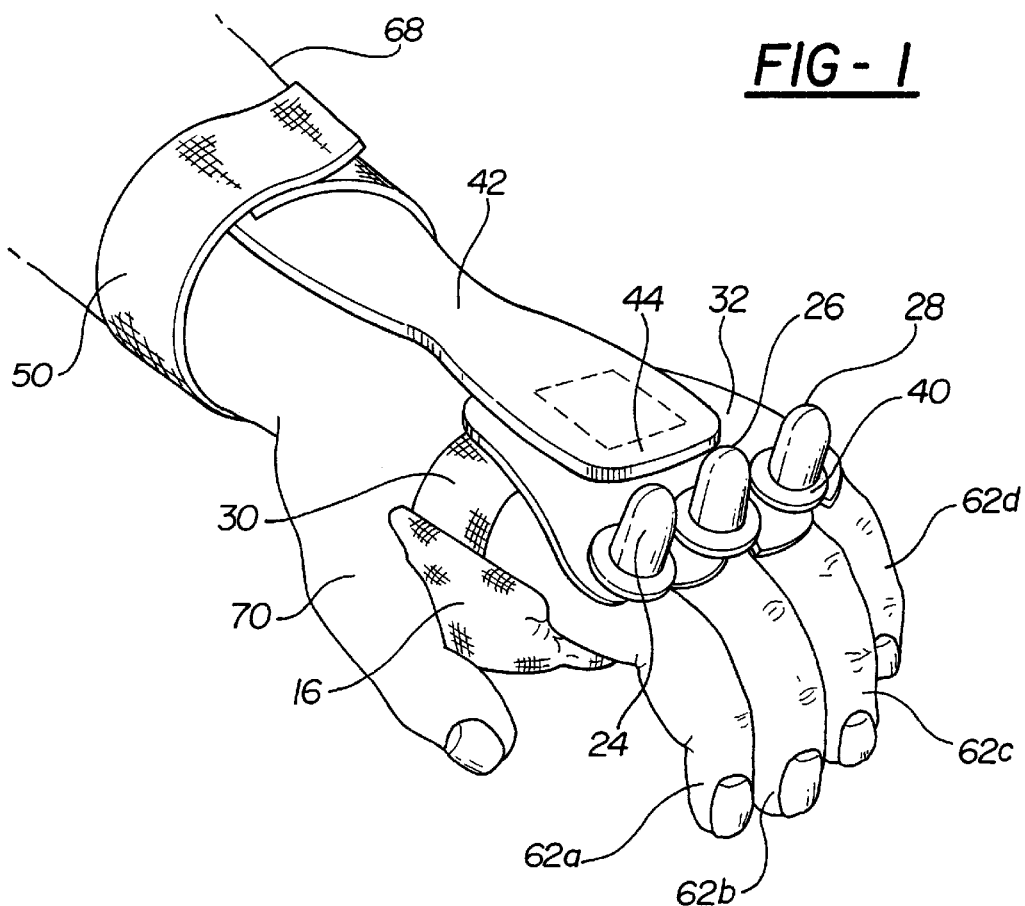
FIG. 1 is a perspective view of the hand splint attached to a person's hand and arm.
Figure 2:
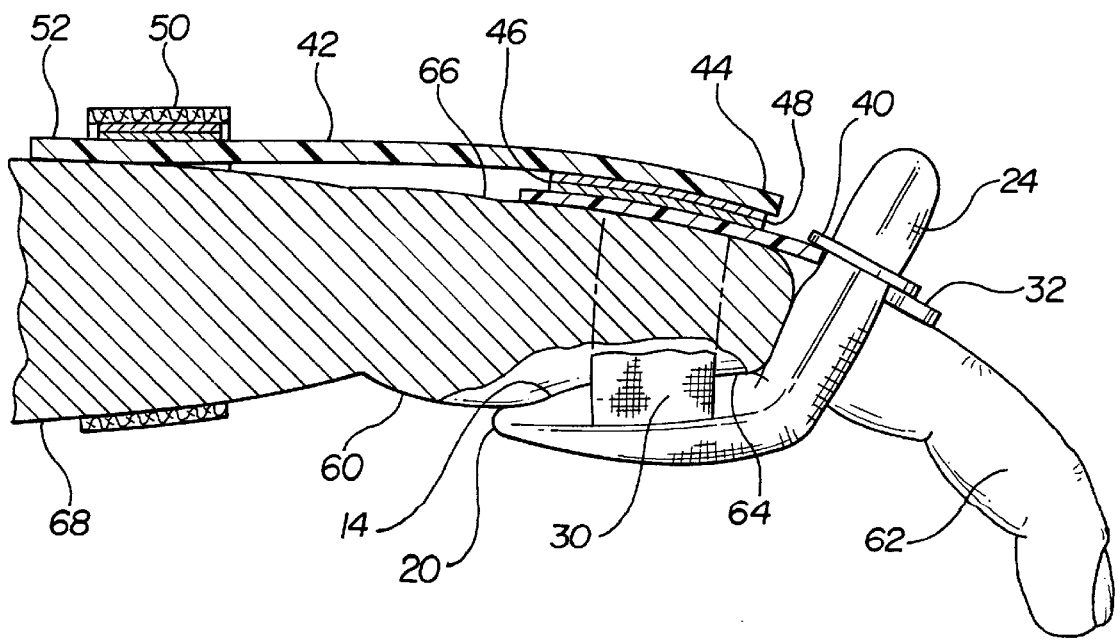
FIG. 2 is a partial sectional view of the hand splint with parts broken away.

The muscle tone reduction splint 10, as shown in FIGS. 1, 2 and 3, is for reducing hypertonicity in the hand. The splint 10 has an elongated pad 12 or palm and finger cushion with an extremity contact surface 14, an inside end 16, an outside end 18, a rear edge 20 and a front edge 22. Three spaced apart elongated and flexible digit separators 24, 26 and 28 or abductor pads, are integral with the elongated pad 12 and extend forwardly from the front edge 22 of the elongated pad. The elongated pad 12 has an outer cover. The outer cover encases a resilient core material. At least the extremity contact surface 14 of the pad 12 and the portions of the outer cover of the flexible digit separators 24, 26 and 28, that are in contact with the volar surface skin of a person using the splint 10, are made from fabric that permits air to reach the skin of the person using the splint.

retainer strap 30 is secured to the elongated pad 12. The strap 30 can be an elastic band with one end fixed to the inside end 16 of the elongated pad 12 and the other end fixed to the outside end 18 of the elongated pad. The strap 30 can also be made from a strip of soft webbing that is secured to the elongated pad 12 and has two free ends. A hook and loop fastener or other adjustable fastener can be used to secure the two free ends.

A dorsal stabilization lid or plate 32 with three slots 34, 36 and 38, passes over the retainer strap 30. The plate 32 is preferably a semi-rigid plastic material that can be fixed to the retainer strap 30 by stitching, an adhesive or by another suitable attaching system if desired. Bands 40 encircle each of the digit separators 24, 26 and 28. Each band 40 is movable along the length of the digit separators 24, 26 and 28 to tighten the splint 10 as explained below. The dorsal stabilization lid 32 has a relieved area 41 over the metacarpophalangeal joints to promote comfort. The lid 32 an also be coated with a soft surface if desired.

A wrist splint 42 is a rigid or semi-rigid member. A forward end 44 of the wrist splint 42 is attached to the plate 32 by a hook and loop fastener or other suitable fastener system. As shown in FIGS. 2 and 3, the fastener system includes a loop pad 46 that is secured to the plate 32 and a hook pad 48 that is secured to a forward end 44 of the wrist splint 42. An arm encircling strap 50 is secured to the rear end 52 of the wrist splint 42. A fastener pad 54 of a hook and loop fastener on the free end of the arm encircling strap 50 engages and is held by a fastener pad 56 on a rear end 52 of the wrist splint 42 and the strap 50. The pads 54 and 56 permit adjustment of the length of the arm encircling strap 50. The pads 54 and 56 could be replaced by other fastener systems that permit adjustment of the effective length of the strap 50.

The muscle tone reduction splint 10 is employed to decrease hypertonicity in the Lumbricale and Palmar interossei muscle groups, while providing stabilization of the metacarpophalangeal joint. The splint is attached to a hand 60 by inserting the fingers 62, 62a, 62b, 62c and 62d between the retainer strap 30 and the elongated pad 12. The pad 12 is positioned against the metacarpophalangeals 64 of the hand 60 adjacent to the fingers 62. The retainer strap 30 passes across the back 66 of the hand 60 adjacent to the metacarpophalangeals 64. The separator 24 is pulled upward between the index finger 62a and the middle finger 62b and forced into the digit separator slot 34. The flexible digit separator 26 is pulled upwardly between the middle finger 62b and the third finger 62c and forced into the digit separator slot 36.

flexible digit separator 28 is pulled upwardly between the third finger 62c and the little finger 62d and forced into digit separator slot 38. The bands 40 are forced onto, or permanently attached to, the flexible digit separators 24, 26 and 28, and into contact with the top of the plate 32 to hold the elongated pad 12 against the metacarpophalangeal joints 64 of the hand 60. In this position the digits or fingers 62 are separated and the fingers are held in an extended and abducted position. In the extended and abducted position, the first phalanx of each finger is nearly aligned with the attached metacarpal bone and the Lumbricale and Palmar interossei muscles are elongated. After the muscle tone of the wrist and hand is reduced, the wrist splint 42 is attached to the plate 32. The arm encircling strap 50 is tightened around the arm 68 and the wrist is held in a more extended position. The inside end 16 of the elongated pad 12 flares between the thumb 70 and the first finger, maintaining the thumb web space. The flexible digit separators 24, 26 and 28 bands 40 hold the plate 32 in place.

The muscle tone reduction splint 10 reduces muscle tone throughout the upper extremity while providing stability at the metacarpophalangeal joint, the dorsum of the hand and the wrist.

Figure 5:
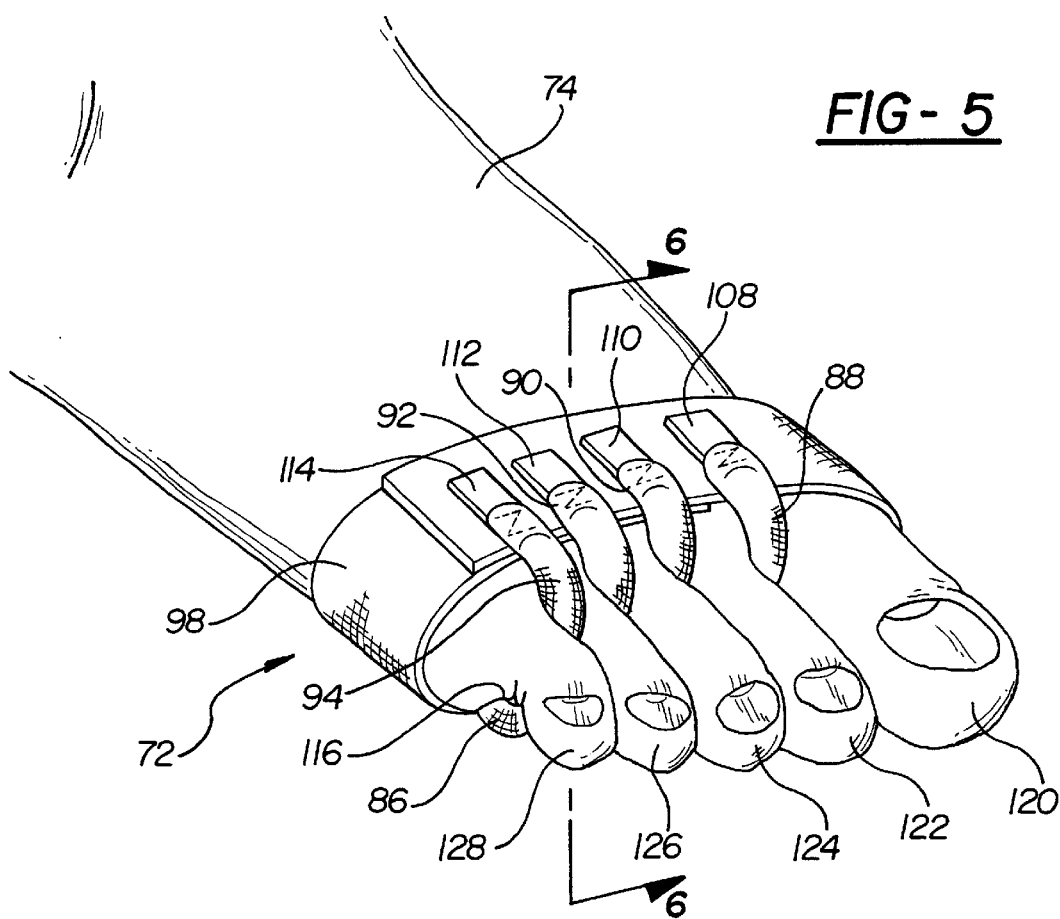
FIG. 5 is a perspective view of the foot splint in use.
Figure 6:
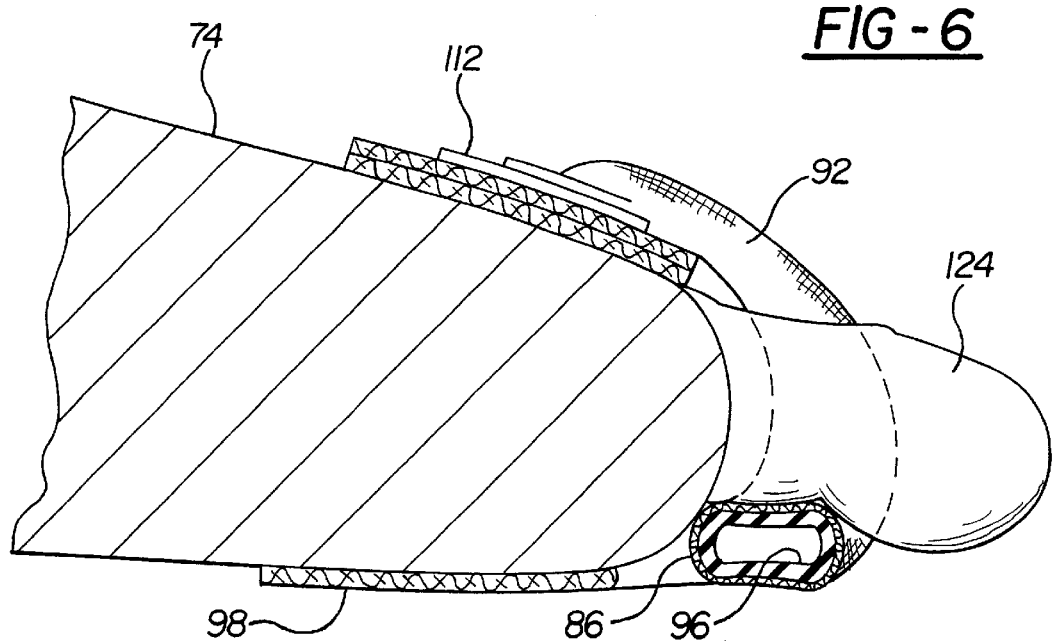
FIG. 6 is a sectional view taken along line 6—6 in FIG. 5.

The muscle tone reduction splint 72, as shown in FIGS. 4, 5 and 6, is for reducing hypertonicity in the toes, foot and ankle. Pressure applied to the metatarsal heads 75 at the metatarsophalangeals results in lower extremity extensor tone being reduced. The splint 72 has an elongated pad 76 with an inside end 78, an outside end 80, a rear edge 82, and a front edge 84. The front edge 84 of the pad 76 is a relatively large diameter and generally cylindrical pad portion 86 that is to be positioned in the toe crease under all of the toes of one foot. Four spaced apart elongated and flexible digit separators 88, 90, 92 and 94 are attached to the front edge 84 of the pad portion 86. The elongated pad 76 and the flexible digit separators 88, 90, 92 and 94 have fabric covers that encases a resilient core material. This resilient core material in the pad portion 86 can be a resilient tube 96. The core material in the digit separators 88, 90, 92 and 94 is preferably one that permits the passage of air to the skin of the foot 74.

A retainer strap 98 is secured to the elongated pad 76 by stitches 100. The ends 102 and 104 of the retainer strap 98 are overlapped but can be butted and secured in place by a hook and loop fastener 106. The other half of the hook and loop fastener 106 is integral with the retainer strap 98. Hook and loop fastener tabs 108, 110, 112 and 114 are secured to the free ends of the flexible digit separators 88, 90, 92 and 94. The other half of the hook and loop fasteners is integral with the retainer strap 98.

The muscle tone reduction splint 72 is employed to relieve pressure at the metatarsal heads and lessen tactile and proprioceptive input to the foot 74, reducing tone in the ankle, foot and toes. The splint is attached to the foot 74 by positioning the large diameter rolled pad portion 86 in the toe crease 116. The retainer strap 98 is then wrapped around the foot 74 as shown in FIG. 5 and secured in place by a hook and loop fastener. The flexible digit separator 88 is pulled up between the great toe 120 and the second toe 122 and secured to the retainer strap 98 by the tab 108. Following the same procedure, the digit separator 90 is pulled up between the second toe 122 and the third toe 124 and secured in place by the tab 110 and the digit separator 92 is pulled up between the third toe 124 and the fourth toe 126 and secured by the tab 112. Finally the digit separator 94 is pulled up between the fourth toe 126 and the little toe 128 and anchored to the retainer strap 98 by the tab 114.

The muscle tone reduction splint 72 holds toes 120, 122, 124, 126 and 128 in an abducted position and provides stabilization at the metatarsal joint. This can result in decreased abnormal tone throughout the lower extremity.

disclosed embodiment is representative of a presently preferred form of the invention, but is intended to be illustrative rather than definitive thereof. The invention is defined in the claims.

We claim:

1. A muscle tone reduction splint for reducing hypertonicity in the Lumbricale muscles comprising:

an elongated pad having an extremity contact surface, a forward edge, an inside end, an outside end and a rear edge;

a plurality of flexible digit separators each of which has a fixed end that is integral with the forward edge of the elongated pad and a free end;

a retainer strap secured to the elongated pad and operable to encircle an extremity adjacent to a base of a plurality of extremity digits;

a digit separator retainer assembly including a semi-rigid plate with a plurality of digit separator slots each of which receives the free end of one of the plurality of flexible digit separators and holds the free end of each of the plurality of flexible digit separators between two adjacent digits; and wherein the semi-rigid plate is attached to the retainer strap.

2. A muscle tone reduction splint as set forth in claim 1 wherein the digit separator retainer assembly includes a plurality of digit separator holders each of which engages one of the digit separators and holds the engaged digit separator in one of the digit separator slots in the semi-rigid plate.

3. A muscle tone reduction splint as set forth in claim 2 wherein each of the plurality of digit separator holders includes a band that encircles one of the digit separators.

4. A muscle tone reduction split as set forth in claim 1 including:

a wrist splint having a forward end secured to the semi-rigid plate and a rear end; and an arm encircling strap secured to the rear end of the wrist splint.

5. A muscle tone reduction splint as set forth in claim 1 wherein the inside end of the elongated pad is sized and configured to separate two of the plurality of digits.

6. A muscle tone reduction splint as set forth in claim 1 wherein the digit separator retainer assembly connects a free end of each of the plurality of flexible digit separators to the retainer strap.

7. A splint for holding each Lumbricale muscle of a hand in an elongated position comprising:

an elongated pad having a hand contact surface, a forward edge, an inside end, an outside end and a rear edge;

a plurality of flexible finger separators integral with the forward edge of the elongated pad;

a retainer strap secured to the elongated pad and operable to hold the hand contact surface of the elongated pad in contact with said hand; and a finger separator retainer assembly including a plate attached to the retainer strap and having three finger separator slots each of which receives and holds one of the plurality of flexible finger separators.

8. A splint as set forth in claim 7 wherein the plurality of flexible finger separators includes an index finger and middle finger separator, a middle finger and third finger separator and a third finger and little finger separator.

9. A splint as set forth in claim 8 wherein the inside end of the elongated pad is sized and configured to separate two of the plurality of digits.

10. A muscle tone reduction splint for reducing hypertonicity in the Lumbricale muscles comprising:

an elongated pad having an extremity contact surface, a forward edge, an inside end, an outside end and a rear edge;

plurality of flexible digit separators integral with the forward edge of the elongated pad;

a retainer strap secured to the elongated pad and operable to encircle an extremity adjacent to a base of a plurality of extremity digits;

a digit separator retainer assembly, that holds each of the plurality of flexible digit separators between two adjacent digits, including a semi-rigid plate with a plurality of digit separator slots each of which receives one of the plurality of flexible digit separators; and wherein the semi-rigid plate is attached to the retainer strap.

11. A muscle tone reduction splint for reducing hypertonicity in the Lumbricale muscles comprising:

an elongated pad having an extremity contact surface, a forward edge, an inside end, an outside end and a rear edge;

a plurality of flexible digit separators integral with the forward edge of the elongated pad;

a retainer strap secured to the elongated pad and operable to encircle an extremity adjacent to a base of a plurality of extremity digits;

a digit separator retainer assembly, that holds each of the plurality of flexible digit separators between two adjacent digits, and including a semi-rigid plate with a plurality of digit separator slots each of which receives one of the plurality of flexible digit separators;

a wrist splint having a forward end secured to the semi-rigid plate and a rear end; and an arm encircling strap secured to the rear end of the wrist splint.

* * * * *